(12) United States Patent
Hollander et al.

(10) Patent No.: US 6,375,464 B1
(45) Date of Patent: Apr. 23, 2002

(54) MICROMECHANICAL SEAL FOR DENTAL IMPLANT SYSTEMS

(75) Inventors: Bruce Hollander; Ingo Kozak, both of Boca Raton, FL (US)

(73) Assignee: BioLok International, Inc., Deerfield Beach, FL (US)

( * ) Notice: Subject to any disclaimer, the term of this patent is extended or adjusted under 35 U.S.C. 154(b) by 281 days.

(21) Appl. No.: 09/669,450

(22) Filed: Sep. 25, 2000

(51) Int. Cl.[7] .................................................. A61C 8/00
(52) U.S. Cl. ..................... 433/173; 403/285; 411/924.1
(58) Field of Search ................................ 433/173, 174, 433/175, 176; 411/8, 333–335, 360, 924.1; 403/282, 285; 285/382.1, 382.2

(56) References Cited

U.S. PATENT DOCUMENTS 5,098,294 A * 3/1992 Lee et al. .................... 433/173
5,328,371 A * 7/1994 Hund ........................... 433/173
5,447,434 A * 9/1995 Shaw ........................... 433/173

* cited by examiner

*Primary Examiner*—Nicholas D. Lucchesi
(74) *Attorney, Agent, or Firm*—M. K. Silverman

(57) ABSTRACT

A micromechanical seal between a first body and a second body is co-axially threadably securable about a portion of the first body. The seal is created by the combination of an annular planar radial surface within the first body; a surface of rotation of the first body disposed radially inwardly of the annular plane surface and defining, within a radial plane of the body, an obtuse angle, relative to the planar radial surface, in a range of about 90.5 to about 92 degrees; and an annular convex radial surface within the second body, such surface fully complemental in radial dimension to the planar radial surface of the first body, the annular convex surface defining a radius of curvature in a range of about 2 to about 8 ten thousandths of an inch, in which upon complete axial threadable securement of the second body into the first body, a region of compression of material forming the convex surface of the second body occurs at a tangent point of the first and second radial surfaces and in which polar alignment between the first and second bodies, during their threadable securement is facilitated by the above defined obtuse angle.

13 Claims, 6 Drawing Sheets

MICROMECHANICAL SEAL FOR DENTAL IMPLANT SYSTEMS

BACKGROUND OF THE INVENTION

The present invention relates to micromechanical seals and, more particularly, to seals of the type having particular utility in the area of dental implants where it is particularly important to effect a durable closure between the abutment and implant portions of a dental implant system. The importance of, and requirement for, such a seal at the interface between the abutment and implant portions arise because of the need to prevent penetration of such interface by bacteria and microscopic debris to which such dental structures are continually subject.

The instant invention is an improvement of the invention of U.S. Pat. No. 5,447,434 (1995) to Shaw. The invention thereby addresses the long felt need in art of dental implants to provide a micromechanical seal at the interface between the abutment and implant portions of a dental system without requirement for the use of chemical adhesives or washer equivalents for the accomplishment of such a seal.

SUMMARY OF THE INVENTION

The instant invention relates to a micromechanical seal between a first body and a second body which is co-axially threadably securable about a portion of said first body. Said seal is created by comprising (a) an annular planar radial surface within said first body; (b) a surface of rotation of said first body disposed radially inwardly of said annular plane surface and defining, within a radial plane of said body, an obtuse angle, relative to said planar radial surface, in a range of about 90.5 to about 92 degrees; and (c) an annular convex radial surface with said second body, said surface fully complemental in radial dimension to said planar radial surface of said first body, said annular convex surface defining a radius of curvature in a range of about 2 to about 8 ten thousandths of an inch, whereby upon complete axial threadable securement of said second body into said first body, a region of compression of material forming said convex surface of said second body will occur at a tangent point of said first and second radial surfaces and in which polar alignment between said first and second bodies, during said threadable securement thread is facilitated by said obtuse angle.

It is, accordingly, an object of the present invention to provide an improved micromechanical seal between bodies having threadably securable surfaces therebetween.

It is another object to provide an improved micromechanical seal between opposing surfaces of components of a dental implant system.

It is a further object to provide a seal of the above type having improved polar registration of the system components.

It is a yet further object to provide an improved means of sealing between abutment and implant portions of a dental system.

The above and yet other objects and advantages of the invention will become apparent from the hereinafter set forth Brief Description of the Drawings, Detailed Description of the Invention and Claims appended herewith.

DETAILED DESCRIPTION OF THE INVENTION

Figure 1:
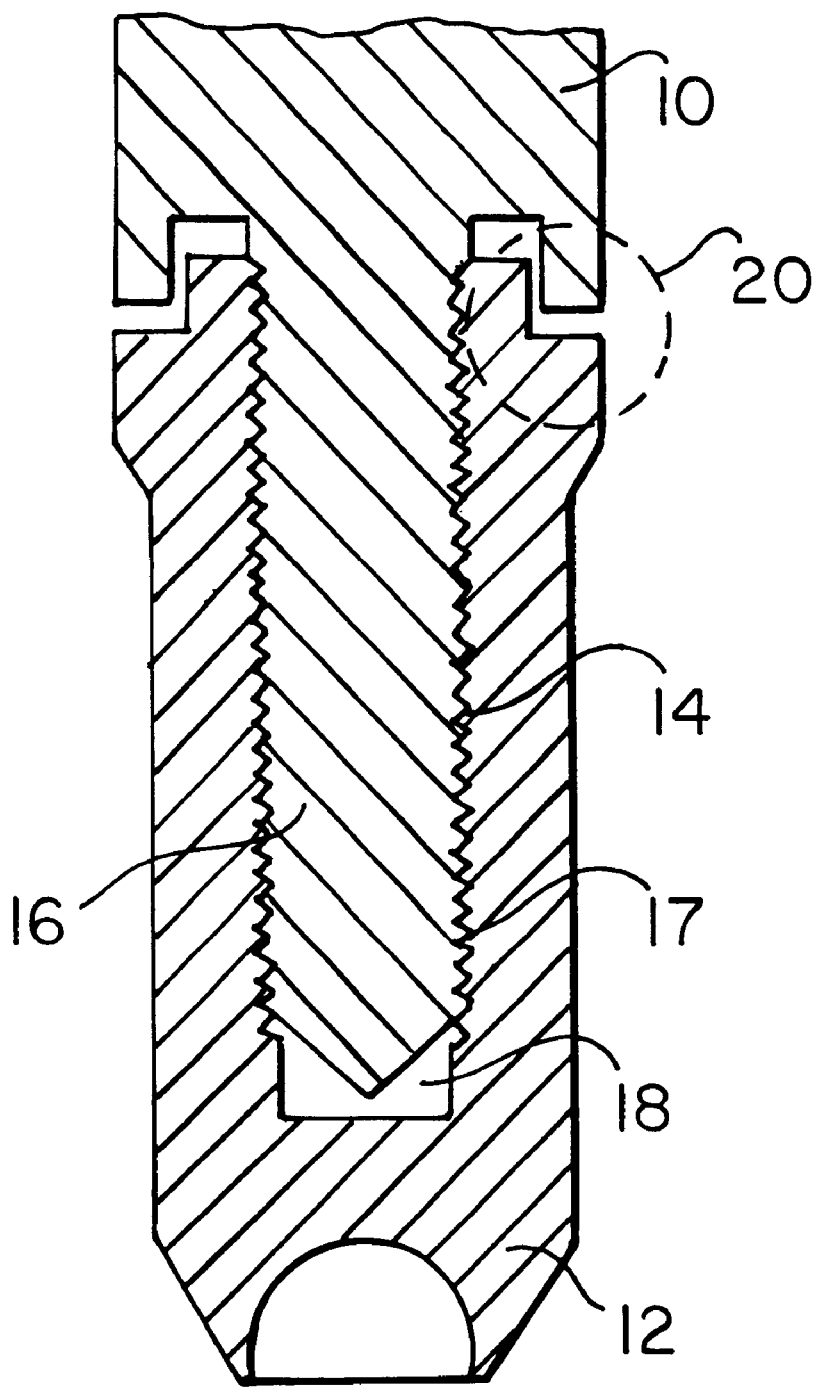
FIG. 1 is an axial cross-sectional view of a prior art dental abutment and implant.

With reference to the axial cross-sectional view of FIG. 1 there is shown a typical prior art dental implant system consisting of an abutment portion 10 and an implant portion 12. Therein, as may be noted, there is provided a first threaded axial surface 14 upon elongate member 16 of abutment 10 and, conversely, a complemental axially threadable surface 17 upon bore 18 of said implant 12. Thereby, in the manner shown in FIG. 1, abutment portion 10 is axially threadably securable into bore 18 of implant 12 along said respectively complementally threadable surfaces 14 and 17.

Figure 2:
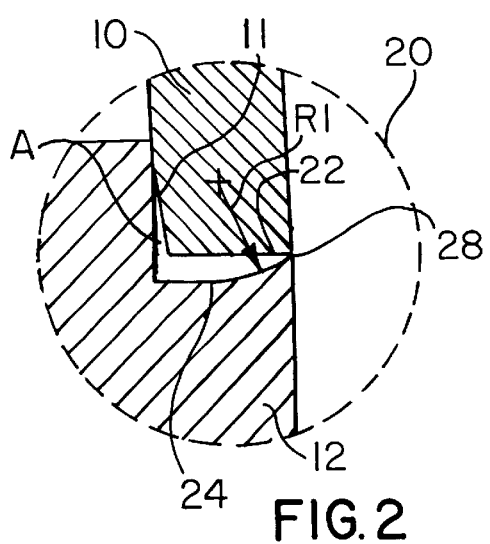
FIG. 2 is an enlarged view of the region of an abutment-implant interface, also shown in dotted circle in FIG. 1 and also showing the improvements of the invention.

In the view of FIG. 1 the respective abutment and implant portions are shown in a partially axially secured condition so that an area of interface 20 between said abutment and implant portions may be viewed in greater detail, with reference to the inventive micromechanical seal in FIG. 2. As may more particularly be noted therein, an annular planar radial surface 22 of abutment 10 is provided. Also shown in FIG. 2 is an axial surface of rotation 11 of abutment 10, such that, in the radial cross-sectional view of FIG. 2, an obtuse angle A is formed between surface 22 and surface 11. This angle is preferable in a range of 90.5 to 92 degrees by preferably 91 degrees.

Figure 3:
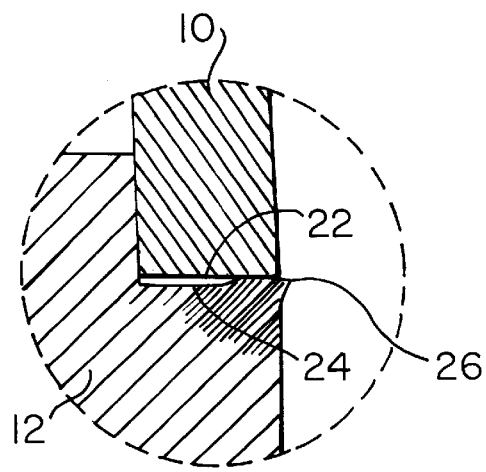
FIG. 3 is an assembly view of FIG. 2 showing in the compressed area of interface of the portions of the implant system.

As may be noted in FIG. 2, an opposing annular radial surface 24 of implant 12 is provided with a concave radius RI which is in a range of two (2) to eight (8) ten-thousandths of an inch. It is noted that the radial and geometries of surfaces 22 and 24 are fully complemental to each other. The result of fully advancing abutment 10 into implant 12, when the surfaces 22 and 24 are contacted, is shown in the view of FIG. 3. Therein, a micromechanical seal 26, caused by material compression at point 28 of FIG. 2, is created. Said seal 26 is characterized by an area of enhanced material density.

Figure 4:
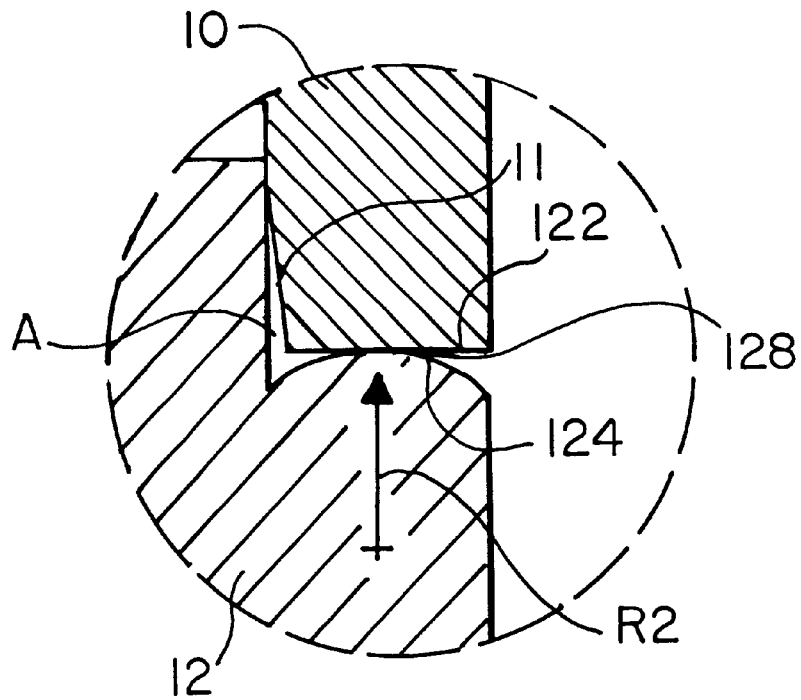
FIG. 4 is a view, similar to the view of FIG. 2, however, showing a second embodiment of the instant invention.

In the view of FIG. 4 is shown a further embodiment of the present invention in which a radius R2 is provided to radial implant surface 124 to create micromechanical seal 126 (see FIG. 5) at point 128, which is a tangent of said surfaces 122 and 124. In this embodiment, the micromechanical seal 126 is formed slightly radially inwardly relative to said seal 26 in the embodiment of FIGS. 2 and 3. The embodiment of FIGS. 4 and 5 also employs the obtuse angle A of the prior embodiment.

Figure 6:
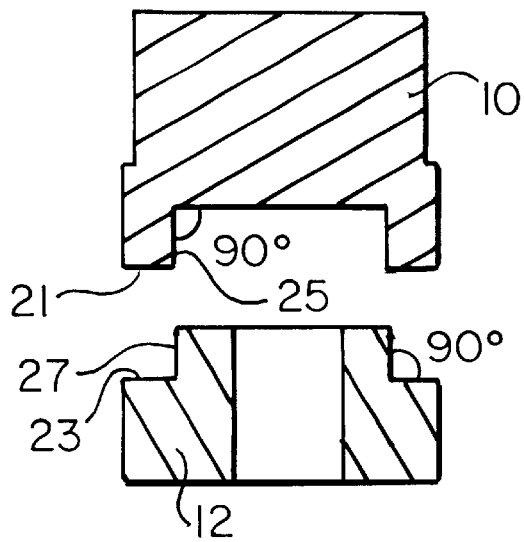
FIGS. 6 to 9 are axial and radial cross-sectional views of the prior art showing the use of vertical surfaces of rotation that are precisely normal to annular radial surfaces of opposing system elements.
Figure 7:
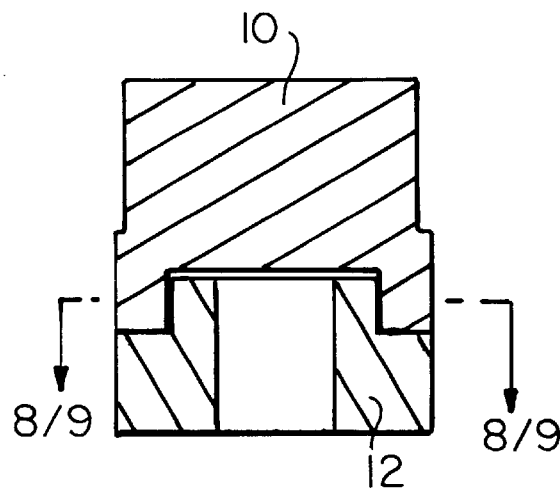
Figure 8:
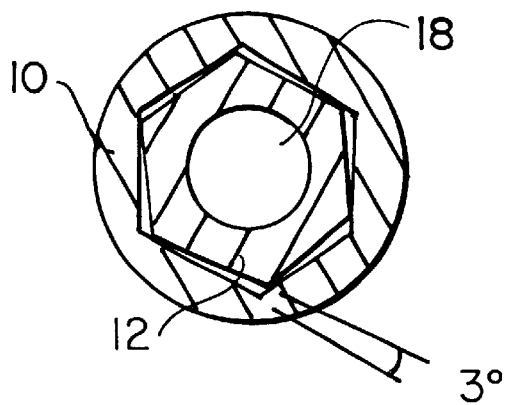
Figure 9:
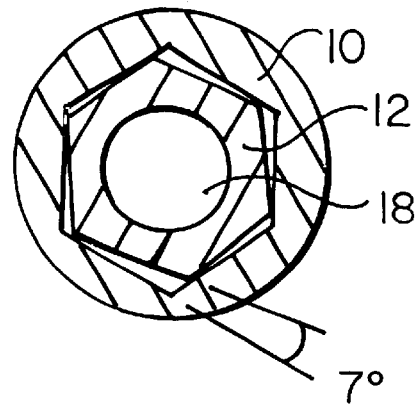
Figure 10:
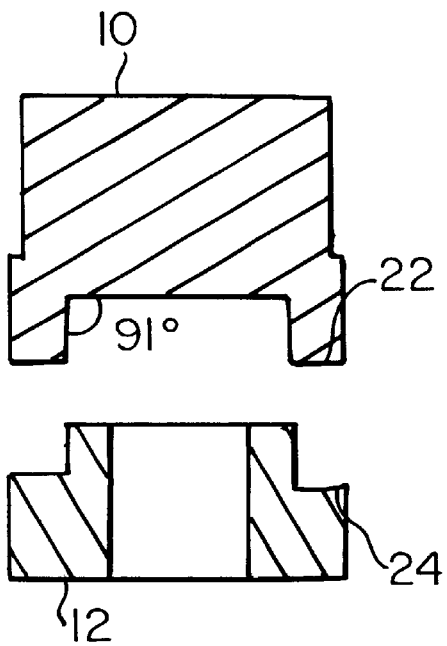
FIGS. 10 to 12 are views, similar to those of FIGS. 7 to 9, however illustrating use of a surface of rotation that is not precisely normal to the radial surface thereof.
Figure 11:
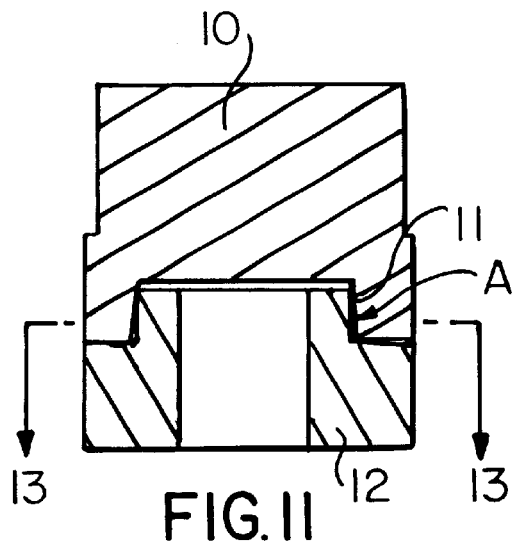
Figure 12:
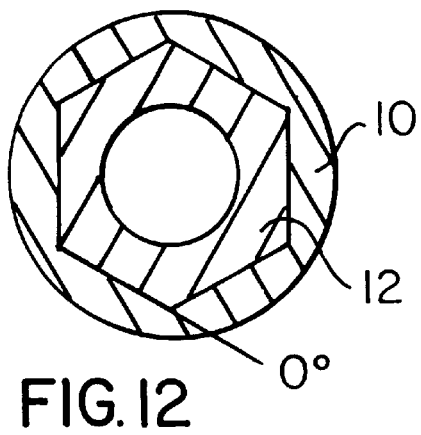

In FIGS. 6 to 12 is more fully shown the polar registration feature of the invention. FIGS. 6 and 7 are prior art exploded and assembly views respectively. FIGS. 8 and 9 are respective radial cross-sectional views taken along Line 8/9 of FIG. 7, which show that the prior art abutment 10 will not accurately register with the implant 12 where radial shoulders 21 and 23 thereof are at exactly a ninety-degree angle (normal) to surfaces of rotation 25 and 27 of the abutment and implant respectively, and that such polar misalignment may be as great as 7 degrees. This effect is believed to be caused by a tendency of the implant dentist to overtorque the abutment. The within inventors have discovered that by providing a slight obtuse, i.e., said angle A (see FIG. 2), such over-torquing can be compensated for to thereby obtain an improvement in polar registration of the components as is shown in FIGS. 10 to 12.

Figure 14:
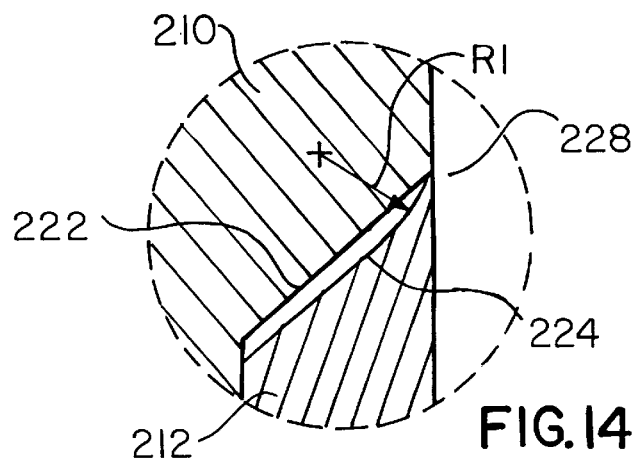
FIG. 14 is an enlarged view of the area of the implant system of FIG. 13 to which the invention is applicable, said view corresponding to the embodiment of FIGS. 2 and 3.
Figure 13:
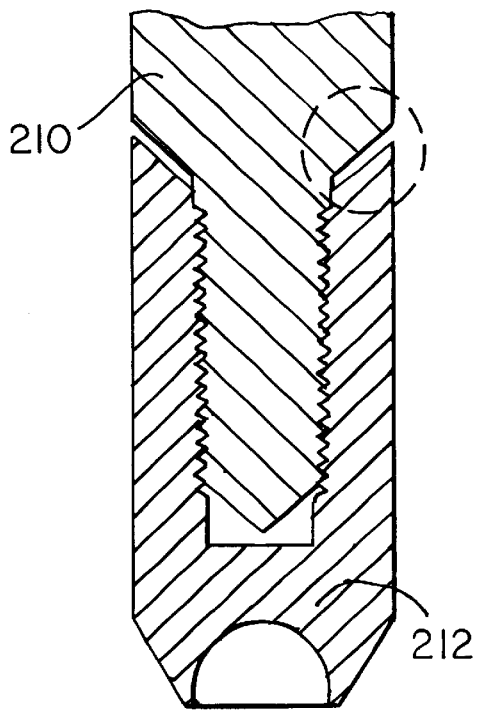
FIG. 13 is an axial cross-sectional view of a form of prior art dental abutment and implant, which employs conical interfaces.

With reference to FIG. 13 there is shown another type of prior art dental system which includes an abutment 210 and an implant 212. Therein, opposing abutment and implant surfaces 222 and 224 (see FIG. 14) are provided; however implant surface 224 is provided with said concave radius R1 discussed above. The principles of operation thereof follow that above-described with reference to the embodiments of FIGS. 2 and 3. Accordingly, at point 228 of FIG. 14, a micromechanical seal is formed after the abutment portion 210 is fully axially secured into implant portion 212.

Figure 5:
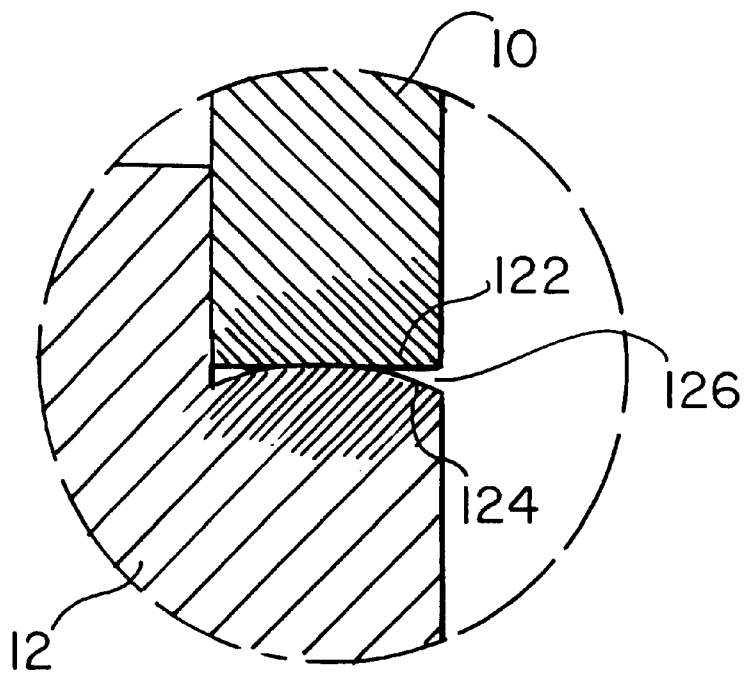
FIG. 5 is an assembly view of FIG. 4 showing the area of compression thereof.
Figure 15:
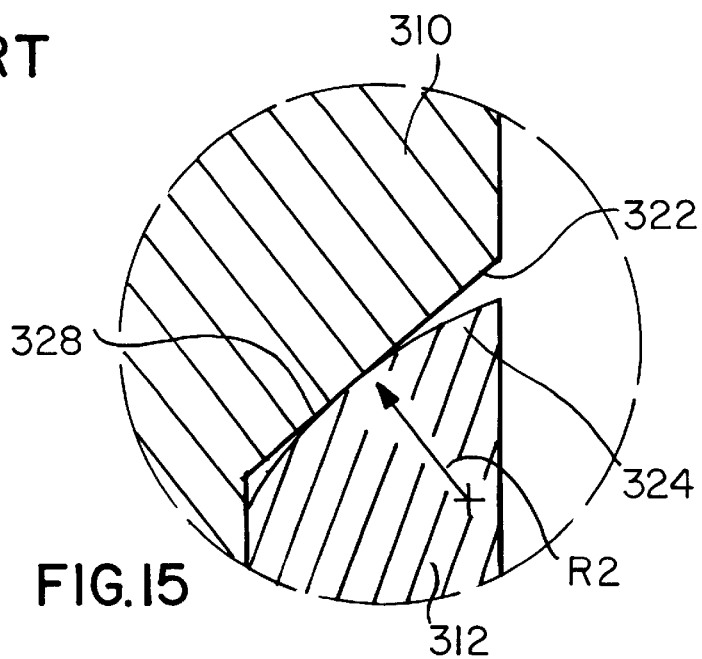
FIG. 15 is an enlarged view of the embodiment of FIGS. 4 and 5 as applied to the implant system of the type of FIG. 13.

In the view of FIG. 15 is shown an embodiment with reference to the prior art structure of FIG. 13 which is similar to the above-described embodiment of FIGS. 4 and 5. Therein opposing surfaces 322 and 324 form a micromechanical seal at point 328 after the portions 310 and 312 have been fully axially secured to each other. Therein, surface 324 is provided with the convex curve R2 of FIG. 4.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

We claim:

1. A micromechanical seal between a first body and a second body which is co-axially threadably securable about a portion of said first body, said seal comprising:

(a) an annular planar radial surface within said first body;

(b) a surface of rotation of said first body disposed radially inwardly of said annular plane surface and defining, within a radial plane of said body, an obtuse angle, relative to said planar radial surface, in a range of about 90.5 to about 92 degrees; and (c) an annular convex radial surface with said second body, said surface fully complemental in radial dimension to said planar radial surface of said first body, said annular convex surface defining a radius of curvature in a range of about 2 to about 8 ten thousandths of an inch, whereby, upon complete axial threadable securement of said second body into said first body, a region of compression of material forming said convex surface of said second body will occur at a tangent point of said first and second radial surfaces and in which polar alignment between said first and second bodies, during said threadable securement thread is facilitated by said obtuse angle.

2. The micromechanical seal as recited in claim 1 in which said first body is a dental implant and said second body in a dental implant, each of a dental abutment system.

3. The micromechanical seal as recited in claim 2 in which said first and second annular radial surfaces comprise frustoconical segments of a virtual cone, thereby defining a virtual acute angle relative to a longitudinal axis of said dental implant system.

4. The seal as recited in claim 2 in which said first and second radial surfaces comprise respective male and female shoulders of said abutment and implant respectively of said dental implant system.

5. The seal as recited in claim 4 in which each of said bodies comprises medical grade titanium.

6. A micromechanical seal between a first body and a second body which is co-axially threadably securable about a portion of said first body, said seal comprising:

(a) an annular planar radial surface within said first body;

(b) a surface of rotation of said first body disposed radially inwardly of said annular plane surface and defining, within a radial plane of said body, an obtuse angle, relative to said planar radial surface, in a range of about 90.5 to about 92 degrees; and (c) an annular concave radial surface with said second body, said surface fully complemental in radial dimension to said planar radial surface of said first body, said annular conave surface defining a radius of curvature in a range of about 2 to about 8 ten thousandths of an inch, whereby, upon complete axial threadable securement of said second body into said first body, a region of compression of material forming said concave surface of said second body will occur at a tangent point of said first and second radial surfaces and in which polar alignment between said first and second bodies, during said threadable securement thread is facilitated by said obtuse angle.

7. The micromechanical seal as recited in claim 6 in which said first body is a dental implant and said second body in a dental abutment, each of a dental implant system.

8. The micromechanical seal as recited in claim 7 in which said first and second annular radial surfaces comprise frustoconical segments of a virtual cone thereby defining a virtual acute angle relative to a longitudinal axis of said dental implant system.

9. The seal as recited in claim 7 in which said first and second radial surfaces comprise respective male and female shoulders of said abutment and implant respectively of said dental implant system.

10. The seal as recited in claim 9 in which each of said bodies comprises medical grade titanium.

11. A micromechanical seal between a first body and a second body which is co-axially threadably securable about a portion of said first body, said seal comprising:

(a) an annular planar surface within said first body, said surface comprising a frustoconical segment of a virtual cone axially centered about an axis of a system defined by said first and second bodies.

(b) a curved annular surface with said second body, said surface fully complemental in radial dimension to said planar radial surface of said first body, said curved surface defining a radius of curvature in a range of about 2 to about 8 ten thousandths of an inch, said surface comprising a frustoconical segment of a virtual cone, complimental to said segment of said planar surface.

whereby, upon complete axial threadable securement of said second body into said first body, a region of compression of material forming said curved surface of said second body will occur at a tangent point of said first and second radial surfaces and in which polar aligmnent between said first and second bodies, during said threadable securement thread is facilitated by said obtuse angle.

12. The seal as recited in claim 11 in which said curved annular surface is convex.

13. The seal as recited in claim 11 in which said curved annular surface is concave.

* * * * *